United States Patent [19]
Wilks, Jr.

[11] Patent Number: 5,608,518
[45] Date of Patent: Mar. 4, 1997

[54] MULTIPLE INTERNAL REFLECTION ANALYZERS NOT REQUIRING EXTERNAL OPTICS

[76] Inventor: Paul A. Wilks, Jr., 179 Middlesex Rd., Darien, Conn. 06820

[21] Appl. No.: 529,371

[22] Filed: Sep. 18, 1995

Related U.S. Application Data

[63] Continuation-in-part of Ser. No. 233,361, Apr. 25, 1994, Pat. No. 5,452,083.

[51] Int. Cl.⁶ .................................................. G01N 21/27
[52] U.S. Cl. ..................... 356/300; 257/416; 257/246; 250/339.12; 250/341.1; 250/341.8
[58] Field of Search ........................ 356/300, 416, 356/419, 244, 246, 445; 250/339.11, 341.1, 339.12, 341.8; 385/12

[56] References Cited

U.S. PATENT DOCUMENTS 3,998,591  12/1976  Eckfeldt ................................. 356/445
4,595,833   6/1986  Sting ..................................... 356/300

FOREIGN PATENT DOCUMENTS 3-291551  12/1991  Japan ..................................... 356/445

*Primary Examiner*—F. L. Evans
*Attorney, Agent, or Firm*—F. Eugene Davis, IV

[57] ABSTRACT

Multiple internal reflection, MIR, rods or internal reflection elements, IRE, use the principal of frustrated total internal reflection, FTIR, (also known as attenuated total reflection, ATR,) in infrared spectroscopy, spectrometers, and spectrophotometers. The rods have polished ends which may be wedges with parallel apexes intersecting the optical axis of the rod. One wedge is convex and the other concave. The concave may be a cone with the axis of the cone coincident with the optical axis of the rod. The angle of the concave wedge or the apex of the cone is slightly greater than twice the critical angle of incidence of the wavelengths to be used for optical analysis incident on the inner surface of the rod when immersed in a material to be analyzed. The angle of the apex of the convex wedge is slightly less than twice 90° minus the critical angle.

20 Claims, 5 Drawing Sheets

MULTIPLE INTERNAL REFLECTION ANALYZERS NOT REQUIRING EXTERNAL OPTICS

RELATED APPLICATIONS

This application is a continuation-in-part of my U.S. application Ser. No. 08/233,361; filed Apr. 25, 1994 entitled MULTIPLE INTERNAL REFLECTION ANALYZERS NOT REQUIRING EXTERNAL OPTICS, now U.S. Pat. No. 5,452,083 which application is incorporated herein by reference.

TECHNICAL FIELD

This invention relates to Multiple Internal Reflection Analyzers Not Requiring External Optics utilizing internal reflection elements providing multiple internal reflection, frustrated total internal reflection, and attenuated total reflection. The invention further relates to infrared spectroscopy, spectrometers, and spectrophotometers. Optical analyzers according to the invention are particularly useful for analyzing fluids, particularly liquids; for example, the carbon dioxide, $CO_2$ content in carbonated water and carbonated beverages.

BACKGROUND ART

Optical analyzers utilizing attenuated total internal reflection are disclosed in my earlier U.S. Pat. No. 3,460,893, Issued Aug. 12, 1969 for APPARATUS FOR ANALYZING A CONTINUOUS MOVING STRIP BY MEANS OF ATTENUATED TOTAL REFLECTION, my United Kingdom Patent No. GB 2,105,058B, Patent published Jan. 8, 1986 entitled FRUSTRATED MULTIPLE TOTAL INTERNAL REFLECTION ABSORPTION SPECTROPHOTOMETER, and my U.S. Pat. No. 5,185,640, Issued Feb. 9, 1993 entitled MULTIFACETED PROBES FOR OPTICAL ANALYSIS which patents are incorporated herein by reference. Each of the above patents discloses internal reflection rods for optical analysis. In the British Patent and the latter U.S. Patent the rods are utilized for analyzing fluids, particularly liquids.

All of these elements and all of the similar elements utilized in the prior art, I believe, have required the use of optical elements, such as lenses or reflecting mirrors to concentrate light from a light source into the elements and to collect the light exiting the elements and direct it to a detector.

Such light concentrating and light collecting optical elements add to the cost of any analyzer using totally internally reflecting rods according to the prior art.

A need exists in the beverage dispensing industry for an inexpensive monitor of the carbon dioxide ($CO_2$) content of carbonated water, for example, as supplied to the multiple soft drink dispensers used in restaurants and bars. The variation in $CO_2$ content is one of the main causes of improper taste in soft drinks.

DISCLOSURE OF THE INVENTION

This invention is an improvement over prior art optical analyzers utilizing totally internally reflecting rods, in that, it dispenses with optical elements for concentrating light from a source on to the rod and for gathering the light from the rod and directing it to one or more detectors.

The invention makes use of an infrared transmitting internal reflection rod having polished ends which may be wedges with parallel apexes intersecting the optical axis of the rod. One wedge is convex and the other concave. The concave end may be a cone with the axis of the cone coincident with the optical axis of the rod. The angle of the concave wedge or the apex of the cone is slightly greater than twice the critical angle of incidence of the wavelengths to be used for optical analysis incident on the inner surface of said rod when immersed in a material to be analyzed. The angle of the apex of convex wedge is slightly less than twice 90° minus the critical angle.

The light source of the invention may be a miniature incandescent bulb or a small nichrome wire mounted on a heat sink, such as diamond, located on the optical axis of the rod and at the intersection of the perpendicular bisectors of the concave wedge surfaces or the legs of the angle formed by the cone and a plane coincident with the optical axis. Thus, if the apex angle of the cone or wedge is less than 90° (as with a cubic zirconia rod), the infrared source will be located within the concave end of the rod.

One or more small detectors are mounted to the surfaces of convex wedge at the opposite end of the rod. Dual detectors may each be located on a bisector of the wedge face facing opposite sides of the wedge.

Filters may be placed directly on the end surfaces where the detector or detectors are located. Alternatively, they may be mounted on the surfaces of the concave end of the rod. A wedge shaped source end is particularly useful for dual detectors, as different filter elements may be mounted on each wedge face and the detectors mounted at the opposite end of the rod.

The material to be analyzed is in optical contact with the surface of the rod, such that total internal reflection takes place in the rod an evanescent wave passes slightly into the material to be analyzed, as is well known in the art.

The invention will be described, with particular reference to fluid analysis, particularly the analysis of the $CO_2$ content of water or carbonated beverages.

OBJECTS OF THE INVENTION

It is therefore an object of the invention to provide totally internally reflecting rods for optical analysis that do not require concentrating or collecting optics.

Another object of the invention is to provide optical analyzers utilizing only a single wavelength for analysis.

A further object of the invention is to provide for the efficient transmission of energy into and out of such rods.

Other objects of the invention will in part be obvious and will in part appear hereinafter.

The invention accordingly comprises the features of construction, elements, and arrangement of parts, which will be exemplified in the constructions herein set forth. The scope of the invention is indicated in the claims.

BRIEF DESCRIPTION OF THE DRAWINGS

For a fuller understanding of the nature and objects of the invention, reference should be had to the following detailed description, taken in connection with the accompanying drawings, in which.

The same reference characters refer to the same elements throughout the several views of the drawings.

BEST MODE FOR CARRYING OUT THE INVENTION

Figure 1:
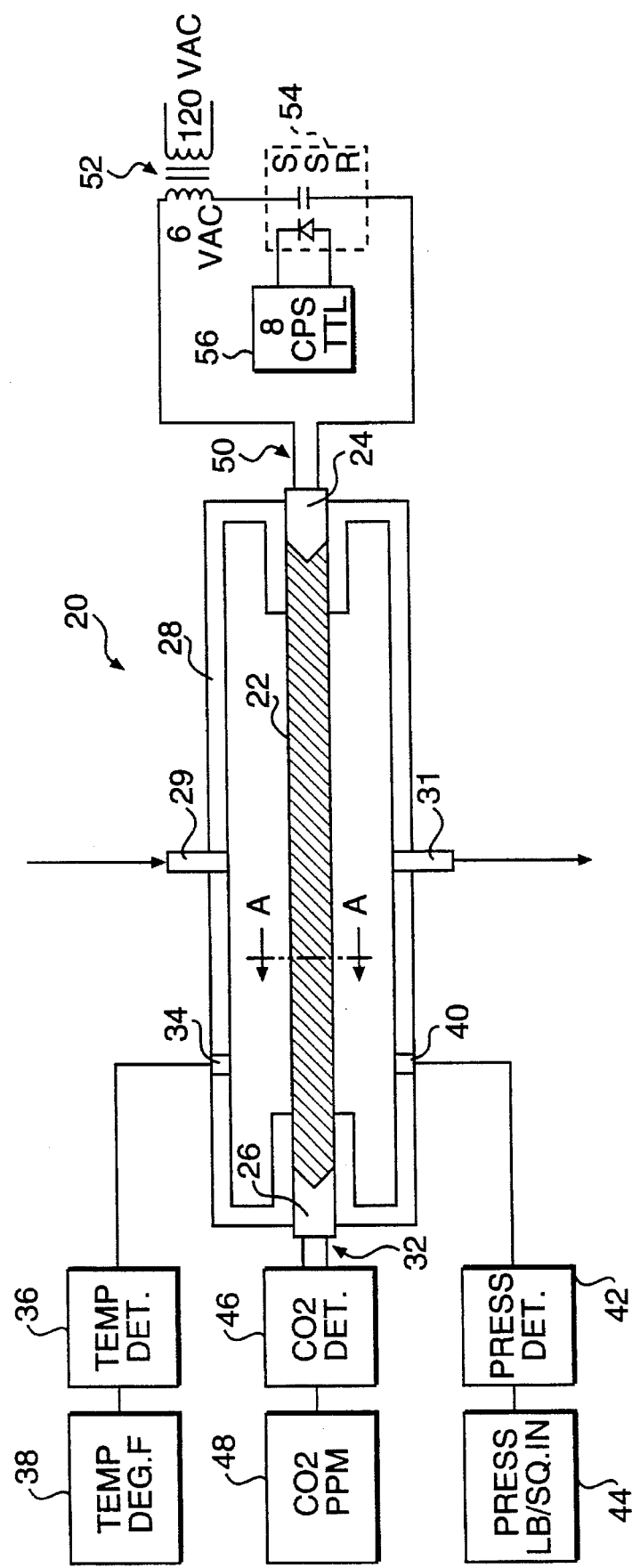
FIG. 1 is a diagrammatic view of a multiple internal reflection optical analyzer according to the invention for measuring a characteristic of a fluid.

Now referring to FIG. 1, a liquid analyzer according to the invention is generally indicated at 20. It comprises totally internally reflecting rod 22 which is transmissive at the wavelengths being used to analyze the liquid. An infrared light source 24 is located at one end of the rod 22. Detectors 26 at the other end. The rod 22 is sealed in a cylinder 28 to which fluid is supplied at inlet 29 and exits via outlet 31. The detectors 26 provide signals on wires generally indicated at 32.

The wires 32 are connected to $CO_2$ detector 46 which indicates $CO_2$ content on display 48. Temperature probe 34 is connected to temperature detector 36 which indicates temperature on display 38. Pressure probe 40 is connected to pressure detector 42 which indicates pressure on display 44. The $CO_2$ content, temperature, and pressure may also be supplied to computers, recorders or control devices for $CO_2$ content, temperature, and pressure.

The light source, which may be a miniature incandescent bulb or heated nichrome wire, is modulated (turned on and off) at 8 cycles per second via wires 50 supplied by transformer 52 and modulated by an 8 cps TTL oscillator 56 switching SSR 54.

Figure 2:
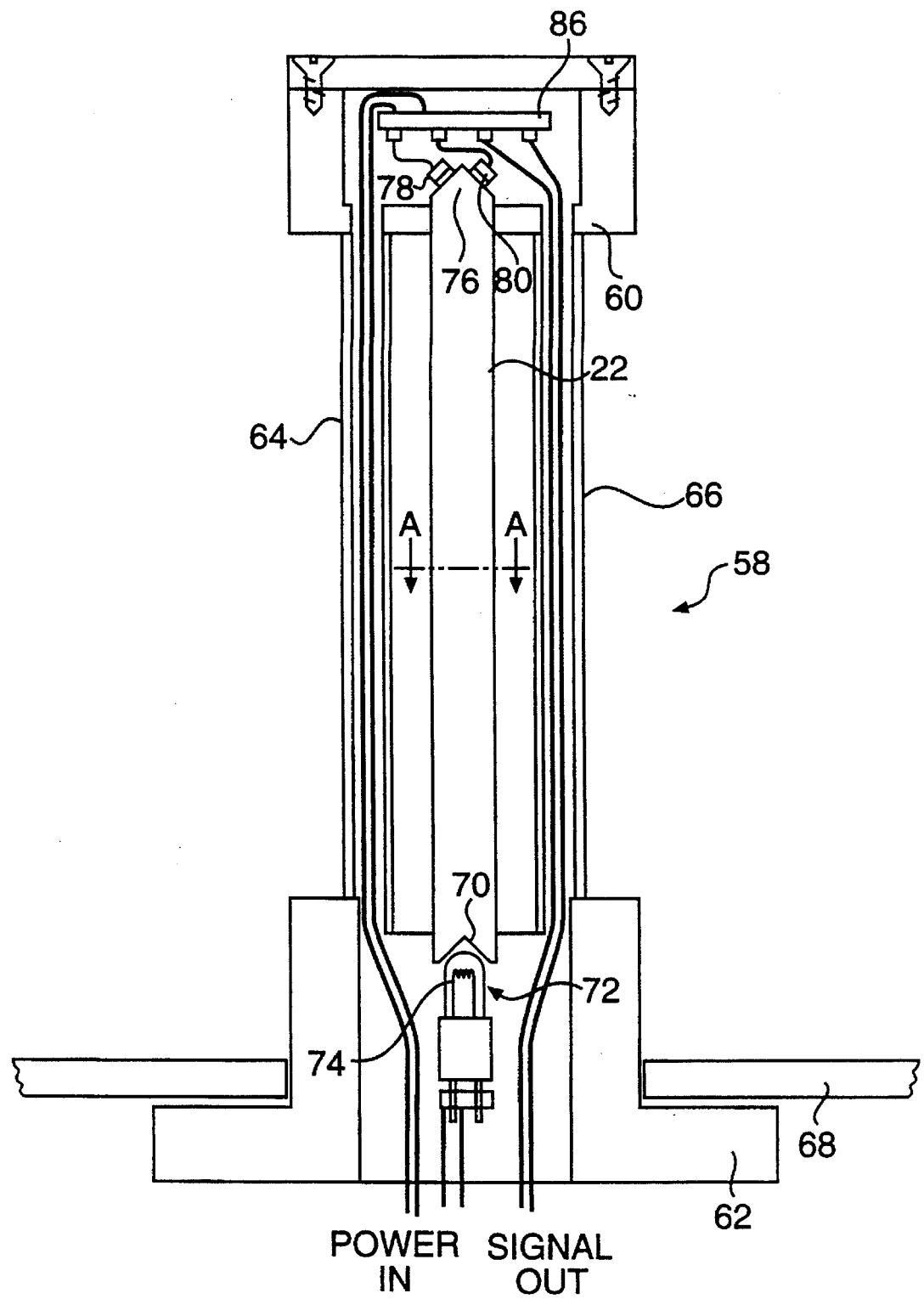
FIG. 2 is a detailed diagrammatic cross-sectional view of the optical system of the analyzer shown in FIG. 1.
Figure 6:
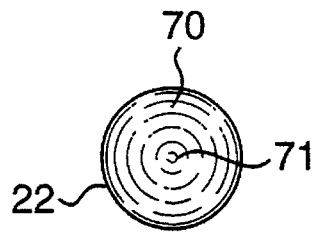
FIG. 6 is a left end view of the multiple internal reflection rod shown in FIGS. 1 and 2.
Figure 7:
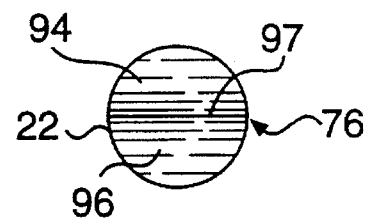
FIG. 7 is a right end view of the rod shown in FIGS. 1 and 2.

Now referring to FIGS. 2, 6, and 7, an inline carbonation sensor is generally indicated at 58. Here the rod 22 is mounted between stainless steel blocks 60 and 62 which are held together by two stainless steel tubes 64 and 66 welded thereto. Block 62 is mounted to a carbonated beverage pipe 68.

Rod 22 has a concave cone 70 into which miniature tungsten lamp 72 is placed with the filament 74 located at the intersection of the bisectors of the legs of the cone as taught in my above-identified patent application.

Rod 22 forms a convex wedge 76 at its other end. Unitary filter detectors 78 and 80 are attached to the wedge faces 94 and 96. A preamp and bias board 86 is mounted in block 60. Wires to and from board 86 pass through tubes 64 and 66. Alternatively, as shown in FIG. 3, the filter detectors 78 and 80 and board 86 may be mounted in a concave wedge shaped housing 88 which is pressed against the wedge shaped end 76 of rod 22.

Figure 3:
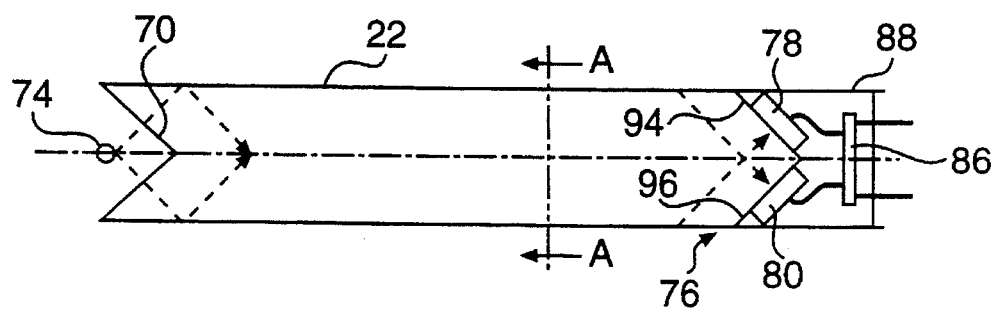
FIG. 3 is a diagrammatic view of an alternative embodiment of the optical system of FIGS. 1 and 2.
Figure 4:
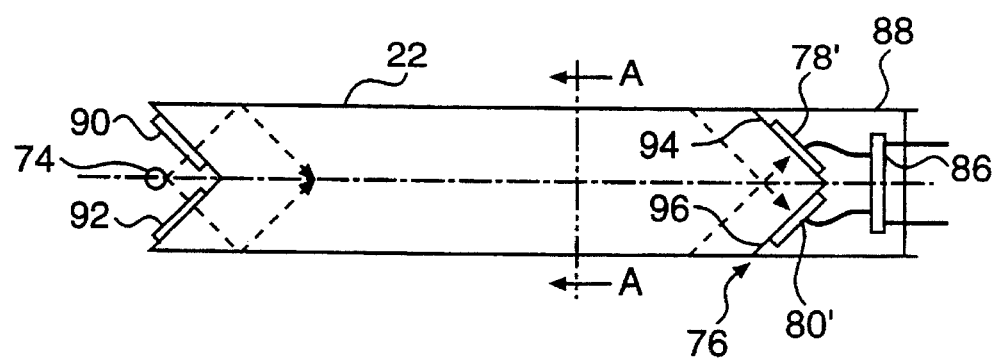
FIG. 4 is a diagrammatic view of another alternative embodiment of the optical system of FIGS. 1 and 2.
Figure 5:
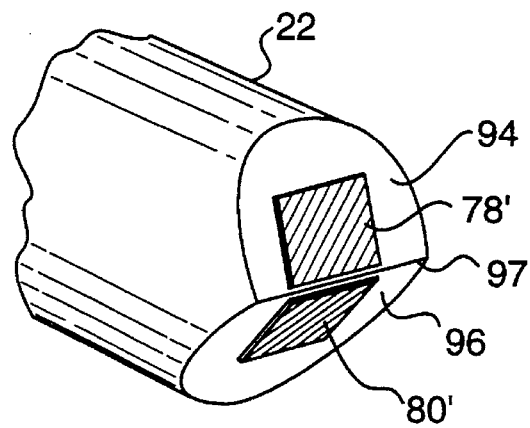
FIG. 5 is a partial perspective view of the right end of the rod shown in FIG. 4.

Alternatively, as shown in FIGS. 3 and 4 filters 90 and 92 may be mounted on the cone and filterless detectors 78' and 80', e.g. lead selenide, may be adhered to the faces 94 and 96 of the rod 22.

Figure 8:
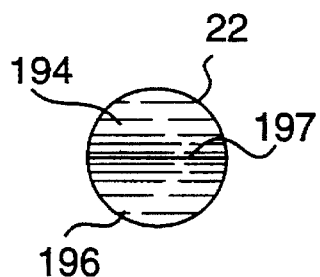
FIG. 8 is a left end view of an alternative embodiment of the rod shown in FIG. 1.
Figure 9:
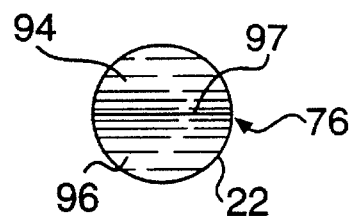
FIG. 9 is a right end view of the alternative embodiment of FIG. 8.

Alternatively, the light source end of the rod 22 may be a concave wedge as shown in FIG. 8 and the detector and a convex wedge as shown in FIG. 9. Here the filters of FIG. 4 would be mounted to the flat surfaces 194 and 196 of the concave wedge.

The detector end may have more than two facets if more than two wavelengths are to be monitored.

The light source 24 is modulated and the signals from the detectors 24 demodulated and processed as disclosed in my earlier above-identified U.S. Pat. No. 5,185,640. The rod 22 may be of the order of 0.5 centimeter in diameter and approximately 7.5 centimeters in length in which case the detectors 24 are approximately 1 milimeter square.

For measuring carbon dioxide, the reference wavelength may be 4.2 micrometers and the analytical wavelength 4.27 micrometers.

Figure 10:
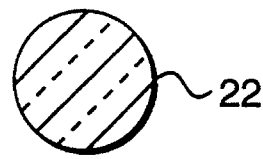
FIG. 10 is a cross-sectional view of the rods of FIGS. 1, 2, 3, and 4 taken along the lines A-A when they are right circular cylinders.
Figure 11:
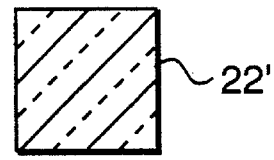
FIG. 11 is a cross-sectional view taken along the lines A—A of FIGS. 1, 2, 3, and 4 of an alternative embodiment of the rods of FIGS. 1, 2, 3, and 4 when they have a square cross section.

The rod 22 is preferably a right circular cylinder as illustrated in FIGS. 1 through 9 and have a circular cross-section at plane A—A in FIGS. 1, 2, 3, and 4 as illustrated in FIG. 10. This is because circular rods are easy to seal with the "O" rings. However, other shapes may be employed. For example, the cross-section A—A may be square as indicated in FIG. 11 in which case the wedge apex 197 shown in FIG. 8 would horizontally bisect the square cross-section shown in FIG. 11 or the conical apex would be in the center thereof.

Figure 12:
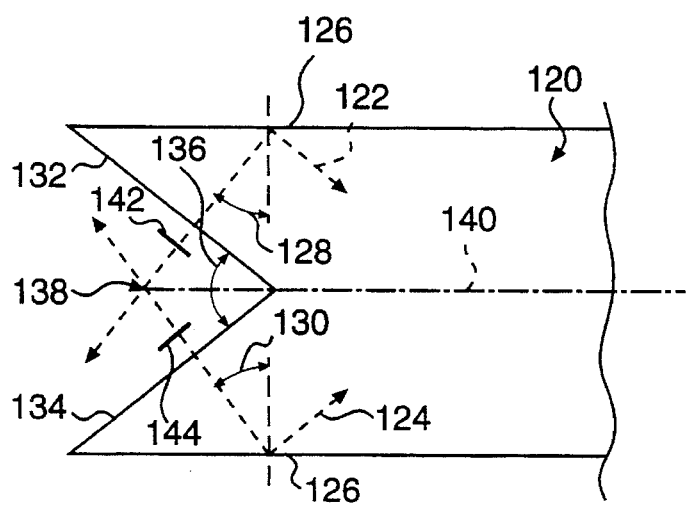
FIG. 12 is a diagrammatic cross-sectional view of the concave end of a multiple internally reflecting rod according to the invention.
Figure 13:
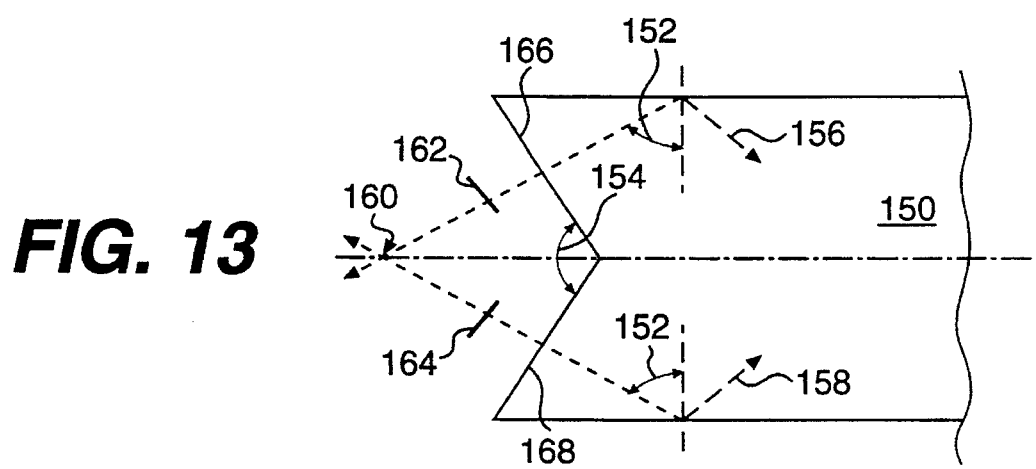
FIG. 13 is a diagrammatic view, similar to FIG. 12, of an alternative rod.

The geometry of the ends of the rods of my invention are illustrated in FIGS. 12 and 13. In FIG. 12, the material of rod 120 and the material to be analyzed cause the critical angle to be some what less than 45°. Thus, the angle at which light rays indicated at 122 and 124 must be incident on the surface 126 of the rod is less than 45° as indicated at 128 and 130. This angle is slightly greater than the critical angle, but must be fairly close to the critical angle as the magnitude of the evanescent wave decreases as the angle of incidence increases. Since the light rays 122 and 124 should penetrate the surfaces 132 and 134, perpendicularly to provide the greatest transmission, from geometry it will be seen that the apex angle 136 is twice the desired angle of incidence 128 and 130 and the rays 122 and 124 cross at a position 138 on the optical axis 140 within the wedge or cone formed by the surfaces 132 and 134.

Thus, with the desired angle of incidence 128 and 130 is less than 45°, the most desired position for the light source is at 138 where the light rays bisect the legs or faces 132 and 134 of the angle forming the wedge or cone, so that the maximum amount of light will be transmitted at the appropriate angle into the rod 120. Similarly, a single detector as illustrated at 110 in FIGS. 6 and 7, would also be located at position 138 in this situation. Dual detectors are mounted such that one faces face 132 and is centered on perpendicular bisector shown by ray 122 and the other faces face 134 on the perpendicular bisector shown by ray 124. Thus, one detector might be located at position indicated by the line 142 and the other indicated by line 144. In this case, both the detectors and the light source are mounted within the concave ends of the rod 120.

FIG. 13 illustrates the situation where the material of a rod 150 and the nature of the material in which it is immersed causes the desired angle of incidence 152 which is slightly above the critical angle to be greater than 45°. In this case, the apex angle 154 being twice the angle 152 is oblique and the central rays 156 and 158 cross at a position 160 which is outside of the concavity forming the angle 154. The light source would preferably be mounted at position 160 and again the detectors indicated at 162 and 164 would be located along the perpendicular bisector of the legs 166 and 168, respectively. Thus, the source is mounted outside the concave end and the detectors may be mounted inside or outside the concave end.

Figure 14:
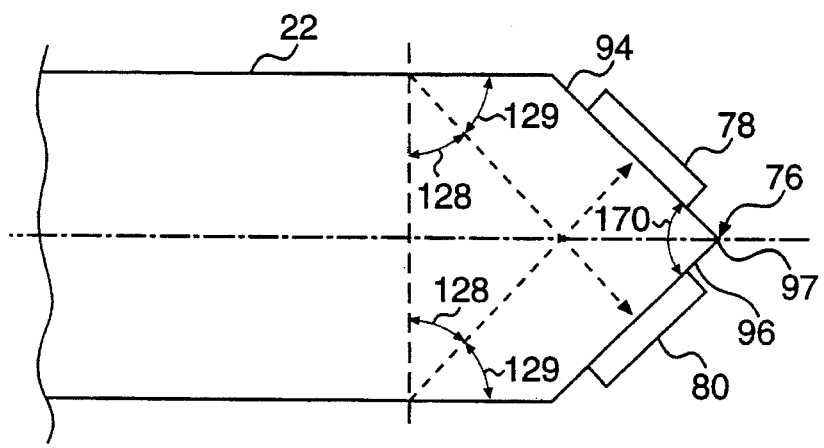
FIG. 14 is a diagrammatic view of the placement of the detectors with respect to a multiple internally reflecting rod as shown in FIGS. 1, 2, 3, and 4.

Now referring to FIG. 14, showing the geometery of the convex wedge end 76 of the rod 22 to which detectors 78 and 80 are affixed. The angle 170 of the apex of the wedge 76 is twice the angle 129 which is 90° minus the angle of incidence 128. Since the angle of incidence is slightly greater than the critical angle for total internal reflection the angle 170 is slightly less than two times 90° minus the critical angle. For a multifaceted rod each facet meets the optical axis 172 at an angle equal to angle 129, that is slightly less than 90° minus the critical angle.

It will thus be seen that the objects set forth above, among those made apparent from the preceding description, are efficently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Having described my invention what I claim as new and desire to secure by Letters Patent is:

1. An optical analyzer comprising:

A) a light source;

B) an electro-optical transducer, which is a detector of a wavelength of light to be used for optical analysis of a material; and, C) a cylindrical rod adapted for immersion in the material to be analyzed having a first and a second end, a cylindrical surface therebetween, and a centrally disposed axis of symmetry intersecting said ends, said first end of said rod being hollowed out to form an end surface which forms an angle having a first pair of legs at the intersection thereof with a plane coincident with said axis, said angle being slightly greater than twice the critical angle of incidence at said cylindrical surface of said rod when immersed in the material to be analyzed at said wavelength, said light source being located substantially on a perpendicular bisector of one of said legs, the second end of said rod is substantially a convex wedge shape having two surfaces meeting at an angle, said electro-optical transducer mounted to receive light passing through one of said wedge surfaces.

2. The analyzer defined in claim 1 wherein said first end of said rod is substantially conical.

3. The analyzer defined in claim 2 wherein said rod is a right circular cylinder.

4. The analyzer defined in claim 1 wherein said first end of said rod is substantially a concave wedge shape having two surfaces meeting at an angle.

5. The analyzer defined in claim 4 wherein said rod is a right circular cylinder.

6. The analyzer defined in claim 4; and,

D) a second electro-optical transducer located substantially on a perpendicular bisector of the other of said end surfaces forming said convex wedge.

7. The analyzer defined in claim 6 wherein said rod is a right circular cylinder.

8. The analyzer defined in claim 6; and,

E) an optical filter on each of said surfaces forming said wedges.

9. The analyzer defined in claim 4; and,

D) an optical filter on said one of said end surfaces.

10. The analyzer defined in claim 1 wherein said light source is located within said hollowed out portion of said first end of said rod.

11. An optical analyzer comprising:

A) a light source;

B) a first electro-optical transducer being a detector of a wavelength of light to be used for optical analysis of a material; and, C) a cylindrical rod adapted for immersion in the material to be analyzed having a first and a second end and a centrally disposed axis of symmetry intersecting said ends, said first end of said rod having a hollowed out portion, said light source being located substantially within said first end of said rod in said hollowed out portion, said second end of said rod being substantially convex and faceted, and said first electro-optical transducer being located to receive light passing through one of said facets.

12. An analyzer defined in claim 11 wherein said transducer is mounted against a facet of said convex end.

13. The analyzer defined in claim 12 wherein said transducer comprises a filter.

14. The analyzer defined in claim 11 wherein there are two facets forming a wedge and the angle of the apex of said wedge is slightly smaller than twice 90° minus the critical angle for total internal reflection in said rod of said wavelength of light.

15. The analyzer defined in claim 11 wherein said first end of said rod is conical.

16. The analyzer defined in claim 11 wherein said first end of said rod is substantially wedge shaped.

17. The analyzer defined in claim 11 wherein said rod is circular in cross section.

18. The analyzer defined in claim 11 wherein said-rod is polygonal in cross section.

19. The analyzer defined in claim 18 wherein said rod is square in cross section.

20. The analyzer defined is claim 19 wherein said first end of said rod is substantially wedge shaped.

* * * * *